United States Patent [19]

Pader

[11] 4,024,239
[45] May 17, 1977

[54] TOOTHPASTE COMPOSITION
[75] Inventor: Morton Pader, West Englewood, N.J.
[73] Assignee: Lever Brothers Company, New York, N.Y.
[22] Filed: July 3, 1975
[21] Appl. No.: 593,080
[52] U.S. Cl. .................................. 424/57; 424/49
[51] Int. Cl.$^2$ ............................................ A61K 7/16
[58] Field of Search ........................... 424/49–58

[56] References Cited

UNITED STATES PATENTS

| | | | |
|---|---|---|---|
| 2,550,207 | 4/1951 | Tainter et al. | 424/49 |
| 3,003,919 | 10/1961 | Broge | 424/49 |
| 3,227,521 | 1/1966 | Carithers et al. | 23/142 |
| 3,538,230 | 11/1970 | Pader et al. | 424/50 |
| 3,670,076 | 6/1972 | Muhler | 424/157 |
| 3,678,155 | 7/1972 | Clippingdale et al. | 424/52 |
| 3,689,637 | 9/1972 | Pader | 424/52 |
| 3,822,345 | 7/1974 | Murray et al. | 424/52 |
| 3,864,470 | 2/1975 | Watson | 424/49 |
| 3,878,938 | 4/1975 | Venables et al. | 206/84 |
| 3,928,541 | 12/1975 | Wason | 423/339 |

FOREIGN PATENTS OR APPLICATIONS 1,559,196  3/1969  France

OTHER PUBLICATIONS

Chem. Abst., 72, No. 15769t (1970) Abst. of FR., 1,559,196, 3/69, Unilever (Toothpaste of a-$Al_2O_3 \cdot 3$-$H_2O$ and PPTD. $SiO_2$).

*Primary Examiner*—Shep K. Rose
*Attorney, Agent, or Firm*—Kenneth F. Dusyn; James J. Farrell; Melvin H. Kurtz

[57] ABSTRACT

A toothpaste composition offering an improved luster to tooth enamel, comprising a mixture of alpha alumina trihydrate and precipitated amorphous silica in combination with a minor amount of anhydrous dicalcium phosphate or dicalcium phosphate dihydrate as a stabilizer.

5 Claims, No Drawings ns at large;
e becomes more
king this character-
oth dentin is a rela-
TOOTHPASTE COMPOSITION

BACKGROUND OF THE INVENTION

The present application is concerned with and relates to a toothpaste composition that has the capacity of imparting a high luster to dental enamel with a lower level of abrasion, and to a composition that can be packed in and dispensed from an uncoated or unlacquered collapsible aluminum tube.

One of the primary objects of a toothpaste is to clean the human teeth. In order to accomplish this result, many toothpaste formulations have been relied upon including the use of solid, particulate, hard particles having abrasive properties. These particles, generally referred to as dentifrice abrasives, must be carefully selected to insure safety as well as efficacy in cleaning. Such particles generally consist of mineral materials: for example, anhydrous or the dihydrate form of dicalcium phosphate, insoluble sodium metaphosphate, silica xerogel, alumina trihydrate, precipitated chalk, and heat-treated calcium pyrophosphate. Other equally important factors that are considered for the selection of the variety of abrasives available include safety, cost, availability, cleaning properties, degree of abrasion, compatibility with other toothpaste ingredients, flavor adsorption characteristics, freedom from impurities and the general feel in the mouth.

While most dentifrice compositions that are currently being marketed seem to satisfy most of the foregoing factors for a properly formulated dentrifrice, two very important features of a toothpaste composition have necessitated a requirement for further improvement, namely, that the toothpaste not be excessively abrasive and at the same time be capable of imparting to the tooth enamel a high luster. The capability of a toothpaste to produce a high luster becomes important since it is not only a measure of tooth cleanliness but also can cause the tooth enamel in vivo to resist staining and the deposition of undesirable oral products such as dental calculus. Most attempts in the prior art towards the fulfillment of these two features have been the provision of dentifrice polishing agents that are in large measure responsible for the scouring and polishing action of the dentifrice. As a result, and in order to obtain an optimum luster effect, it was heretofore necessary to carefully balance the abrasive and polishing characteristics of the polishing agent or add small amounts of specific polishing aids.

Accordingly, the dentifrice formulation art has reached a state of sophistication such that it is known to mix different dentifrice abrasives with each other or with specific additives, to hopefully obtain the beneficial effects, either additively or synergistically.

Thus, U.S. Pat. No. 3,060,098, a polishing agent system is disclosed combining anhydrous alpha alumina with various calcium abrasives such as calcium pyrophosphate and dicalcium phosphate dihydrate. Unfortunately, however, it has been determined that these calcium abrasives, specifically dicalcium phosphate dihydrate, will yield and offer low luster values when present in a toothpaste in significant amounts.

Another example is disclosed in U.S. Pat. No. 3,538,230 wherein a particularly desirable dentifrice is obtained by blending a silica xerogel and a silica aerogel. These products, however, proved to be relatively costly because of the nature of the process for making them. Balsam and Sagarin, Cosmetics, Science and Technology, Second Addition Vol. 1, pages 423 to 531 also provide many examples showing different abrasives in dentifrice compositions, for example, insoluble sodium metaphosphate and dicalcium phosphate, calcium carbonate and dicalcium phosphate dihydrate, and insoluble sodium metaphosphate and calcium pyrophosphate. All of these abrasive systems have been shown to be either higher than necessary in abrasiveness and/or provide little or no lusterizing effects when incorporated into a toothpaste.

In order to familiarize the reader with a standard of reference, luster values have been determined for a number of commercial dentifrices. These luster values are given in the following table with reference only to the abrasive system employed:

TABLE 1

| Abrasive System | Luster Value |
| --- | --- |
| Calcium pyrophosphate | 46–49 |
| Dicalcium phosphate dihydrate plus minor amount of chalk | 48–51 |
| Chalk | 37 |
| Silica xerogel plus silica aerogel | 56–58 |
| Insoluble sodium metaphosphate | 53 |

It becomes apparent that the luster value is quite variable, depending on the abrasive system utilized. It should be pointed out that in terms of the test described in the Examples hereinafter for measuring luster, a superior result is obtained with an abrasive system having a luster value approaching 60, although it has not been found possible to polish tooth enamel to a higher value by conventional and practical procedures.

Examples of other polishing agents or polishing systems in dentifrices may be found in U.S. Pat. No. 3,804,946. The polishing agents therein are included in the class of abrasive polishing systems above in that they suffer from the same drawbacks and disadvantages.

An additional characteristic of a toothpaste composition is the extent to which it abrades the tooth structure, especially the tooth dentin, which may be exposed to a greater or lesser degree in the population at large; excessive exposure of dentin generally becomes more prevalent as people age, thereby making this characteristic even more important. The tooth dentin is a relatively soft structure, in contrast to the very hard tooth enamel. Excessive abrasion of the dentin, therefore, should be avoided. Accordingly, the ideal toothpaste will abrade tooth dentin no more than is necessary to insure that the tooth enamel is free of stain and other undesirable accretions. The literature of dental research has shown that a relationship exists between the ability of a toothpaste to abrade dentin and to clean the tooth surface. This relationship provides a means for measuring the ability of a toothpaste to clean the tooth surface within safe limits of abrasion.

The toothpastes commonly marketed show dentin abrasion values ranging from about 300 to about 700 as determined by the method set forth below. As the value for a given abrasive system increases, the more abrasive that system will be to tooth dentin. In brief, this method comprises making tooth dentin radioactive and abrading the radioactive dentin with toothpaste and toothbrush under standardized conditions. Different abrasive systems show more or less a capability to abrade tooth dentin, as is demonstrated in the following Table 2, wherein dentin abrasion values are given for various comercial toothpastes. Only the abrasive systems themselves are indicated.

TABLE 2

| Abrasive System | Dentin Abrasion Value |
| --- | --- |
| Calcium Pyrophosphate | 568-599 |
| Dicalcium Phosphate Dihydrate plus minor amount of chalk | 290 |
| Chalk | 528 |
| Silica Xerogel plus Silica Aerogel | 487 |
| Insoluble Sodium Metaphosphate | 603 |

The values given for a toothpaste do not necessarily reflect quantitatively the values that would be obtained if one were to use equal weights of abrasive components in a given system. It is apparent, then, that the ideal dentifrice would have as low a dentin abrasion value as is consistent with an efficient cleaning of teeth. There is no reason to believe that exceeding a dentin abrasion value of above about 500-600 would result in any important improvement in tooth cleaning efficiency for a toothpaste. The toothpaste composition according to the invention herein, therefore, is limited to an abrasion value below about 600, and preferably below about 500, as determined by the technique set forth below.

Another important factor that will govern the formulation of a low-cost, economical toothpaste composition is the container that will dispense the toothpaste for consumer use. One of the least expensive containers for toothpaste is the collapsible aluminum tube. This tube is prreferred over other types of tubes for reasons other than cost, that is, it is easy to squeeze the toothpaste out of the tube for consumption. In addition, the filling and sealing operations are less complicated, thereby reducing manufacturing costs.

In connection therewith, most abrasives have the common characteristic of being relatively inert, and are, therefore, generally compatible with the commonly and generally used ingredients of a toothpaste composition, that is, the humectants, flavors, surface active agents, sudsing agents, and binders. Despite this relative inertness, however, abrasives do not retain enough chemical inertness to prevent interactions with the other toothpaste ingredients. This will often lead to many undesirable side effects, among which can be interactions with therapeutic agents leading to the inactivation of the latter; interactions with the toothpaste excipients leading to the generation of gas or the separation of liquid and the resultant destruction of the viscous paste appearance and flow property of the toothpaste; and more importantly interactions with the toothpaste tube itself. For these reasons it is not uncommon to find that many dentifrices are formulated with a stabilizing agent or in the alternative are packed in tubes that are either non-reactive with the the dentifrice or lined with a coating that is not reactive with it.

Nevertheless, the aluminum tube is generally the container of choice and many patents have issued on the formulation of dentifrices developed specifically to allow packaging in this type of tube. Indicative thereof is U.S. Pat. No. 3,678,155, which disclosed a milled alpha alumina trihdrate as a toothpaste abrasive stabilized by a compound that offers orthophosphate ions, for example, dicalcium hydrogen phosphate. It has been determined, however, that such dentifrices containing only alumina trihydrate of the particle size set forth therein for effective cleaning possess a luster-producing capability that is rather low. While this particular patent shows stabilization of a toothpaste composition in unlacquered aluminum tubes, it does so at the expense of the flavor of the toothpaste as well as the luster. Other examples of stabilizing systems may be found in U.S. Pat. No. 3,227,618 and in U.S. Pat. No. 3,678,155. In addition, U.S. Pat. No. 3,683,065 discloses a liquid dentifrice containing aluminum hydroxide as a cleaning agent and dicalcium phosphate dihydrate as a polishing agent. This combination at the levels indicated possesses a relatively high degree of abrasiveness. Furthermore, dicalcium phosphate dihydrate dentifrices containing substantial amounts of alumina trihydrate, as well as high levels of the dicalcium phosphate compound, generally fail to impart significantly high lusters to tooth enamel.

In view of the above, it is desirable, and, therefore, an object of the present invention, to provide a toothpaste composition that will impart a very high luster to tooth enamel and at the same time provide efficacy in cleaning attendant with low abrasiveness.

Still another object of the invention is to provide a toothpaste formulation that can be packed in an unlined collapsible aluminum tube.

Another object of the invention is the provision of a toothpaste formulation that is reasonably low cost and economical, and at the same time compatible with the flavor and other toothpaste ingredients therein.

It has been found, and unexpectedly so, that a toothpaste composition comprising a mixture of alpha alumina trihydrate and precipitated amorphous silica, in combination with a minor amount of either anhydrous dicalcium phosphate or dicalcium phosphate dihydrate as a stabilizer, accomplishes the foregoing objects accompanied by a superior luster-producing capability and a high degree of stability when incorporated into unlined or uncoated aluminum tubes.

In accordance with the toothpaste composition herein, the alpha alumina trihydrate and precipitated amorphous silica are admixed in such proportions as to obtain a high luster and an acceptable but comparatively low level of abrasion for cleaning. This is accomplished by incorporating from about 0.5 to 3 parts of alpha alumina trihydrate with about 1 part of precipitated amorphous silica. This polishing/cleaning system is combined with conventional toothpaste ingredients, namely, flavor, surface active agents, humectants, binders, preservatives, thickeners, and if desired, colors or pigments and water. These ingredients show the properties conventionally attributed to them in the dentifrice literature, and are fairly well known.

As hereinbefore stated, dentifrices or toothpastes containing only alumina trihydrate as the polishing agent do not provide a high luster; in fact, their luster-producing capability is rather low. In addition, the alpha alumina trihydrate of the type herein can be more abrasive to tooth dentin than most of the commonly used abrasives, and only a relatively small amount of the abrasive should be incorporated into a toothpaste if it is to have a comparatively low dentin abrasion value. The degree of abrasion will generally vary with the ratio and absolute amount of the alpha alumina trihydrate in the formulation, as it indeed will vary with virtually all abrasive systems; stated simply, the abrasion will tend to increase as the level and particle size of the abrasive(s) in the dentifrice or toothpaste increases. Thus, the greater the amount of alpha alumina trihydrate present in a toothpaste, the greater the dentin abrasion will be.

In view of the above, it has been found that the maximum level of alpha alumina trihydrate, as characterized below, should generally not exceed 30% when present in the total toothpaste formulation, since higher levels will tend to abrade the dentin to an extent not required for adequate cleaning. On the other hand, a relatively small amount of alpha alumina trihydrate will tend to provide the toothpaste with very poor organoleptic qualities, such as flavor release, body in the mouth, etc. Therefore, in order to formulate a toothpaste with the excellent cleaning of alpha alumina trihydrate as the major abrasive, at a relatively low level, it was found that the incorporation of a relatively inert precipitated amorphous silica at a relatively high level in terms of the total toothpaste composition, cured the organoleptic deficiencies and at the same time produced a superior luster capability to the combination. It, therefore, became possible to provide a stable, organoleptically acceptable, low-abrasion toothpaste based on an alpha-alumina trihydrate cleaning abrasive.

It has been known, however, that dentifrices containing alpha alumina trihydrate or silicas, present problems of stability when stored in uncoated collapsible tubes. Gassing and attack on the internal wall of the aluminum tube occurred during storage. Several suggestions towards stabilizing these dentifrices have been proposed including the addition of minor amounts of soluble phosphate salts. The addition of these salts prevented the product deterioration, but did so at the expense of introducing into the dentifrice a salty, undesirable taste, since these particular phosphate salts were relatively soluble.

Thus, by the addition of dicalcium phosphate dihydrate or anhyrous dicalcium phosphate to the toothpaste system in question, the deterioration of the paste as well as the aluminum tube could be prevented.

Unfortunately, any significant amount of dicalcium phosphate dihydrate or anhydrous dicalcium phosphate in combination with the alpha alumina trihydrate alone or a silica material caused a significant decrease in luster of tooth enamel. Moreover, it was found that alpha alumina trihydrate possessed an unnecessarily high degree of abrasiveness when combined with a relatively large amount of anhydrous dicalcium phosphate, since this material is extremely abrasive because of its high level of hardness. The dicalcium phosphate dihydrate is not considered too abrasive when present in relatively large amounts with the alpha alumina trihydrate, but does possess a low luster-producing capability.

In accordance with the invention, therefore, and in view of the above findings, it has been found that a toothpaste composition comprising 10 to 30% of alpha alumina trihydrate, preferably 20 to 25%, and about 10 to 20% precipitated amorphous silica, preferably 10 to 15%, in combination with a stabilizing agent consisting of about 1 to 5%, or optimally about 1 to 2%, by weight of dicalcium phosphate dihydrate or about 1 to 2%, desirably about 1 to 1.5%, by weight anhydrous dicalcium phosphate, produces a paste, when combined with other ingredients, that is very stable when incorporated into unlined aluminum tubes, relatively inexpensive to manufacture and package, and which produces a superior lusterizing and cleaning effect to the teeth.

The alpha alumina trihydrate employed in the toothpaste composition herein is one that should have an average particle size of about 6.5 to about 8.5 microns, and a screen analysis of all material through 325 mesh. This particular form of the alumina trihydrate is readily available from manufacturers such as The Aluminum Corporation of America under the name hydrated alumina C-331. This alumina is typically employed in the presence of very minor trace amounts of impurities, that is, less than 0.6% of compounds such as ferric oxide, silicon dioxide, and sodium salt. It should be emphasized that the alumina trihydrate that is preferred for the toothpaste herein is one that is relatively chemically pure.

The silica employed in accordance with the invention is a precipitated amorphous silica and is generally and readily available from the J. M. Huber Company under the trademarked name Zeofree 153. The particular silica employed herein is one that should contain a very low abrasive capacity, and a particularly suitable silica is one that has a surface area of 100-140 square meters per gram. This particular silica inherently has a low abrasive capability.

While not desiring to be held to any particular theory, it is believed that the critical nature of the low level of dicalcium phosphate dihydrate or anhydrous dicalcium phosphate on the alpha alumina trihydrate and precipitated amorphous silica is due to the fact that phosphate compounds exert a small but finite solubility in the dentifrice system, and, therefore, provide that amount of phosphate ion required to counteract the factors responsible for dentifrice breakdown and tube attack. It is theorized that the stabilizing agents herein act a a reservoir for the release of the phosphate ion and thereby release phosphate as the reaction causing the adverse stability behavior, intensifies, or alternatively it may well be that it provides that amount of phosphate ion needed to inhibit the reaction before it has a chance to proceed. The former hypothesis is the more likely explanation, since very low levels of added soluble phosphate do not cause the desired degree of inhibition of deterioration.

The following specific Examples are further illustrative of the nature of the present invention. The compositions are prepared in the usual manner by well-known techniques in the art and all amounts of the various ingredients are by weight unless otherwise specified.

In the Examples illustrating the toothpaste composition of the invention set forth below, the following test procedures were employed to deterine luster and dentin abrasion:

LUSTER TEST

The standardized luster test to evaluate ability to improve tooth luster was carried out as follows:

The labial surface of an extracted human central incisor was smoothed with sandpaper, ending with fine grade sandpaper, followed by levigated alumina, and then dulled by buffing with a slurry of chalk. The enamel surface then contained pits chracteristic of a chalk-dulled surface. The degree of dullness was carried to a uniform low reflectance level as measured by a standarized light source-photocell assembly. The tooth was then brushed with the test composition on a standardized brushing machine for a period of two hours, after which the luster was again measured. The luster increase represents the difference between the prebrushing luster figure and the figure obtained after brushing with the test dentifrice, and is the average of the luster increase obtained on three different teeth. The measurement of lusterof any one tooth is accurate within one unit.

DENTIN ABRASION TEST

A. Selection and preparation of teeth

Sound, single-rooted permanent teeth that are caries-free and vital at extraction are selected. Teeth are then scraped clean with a scalpel. The crown and root tip of each tooth are removed using an abrasive disc so as to prepare a dentin sample 14 mm long and at least 2 mm wide at the narrower end. Cut pieces of root are also prepared to be later used in determining a correction factor for self-absorption of radiation.

B. Irradiation of dentin

The prepared roots and dentin chips described in Step A are exposed to a neutron flux of $2 \times 10^{12}$ neutrons/cm$^2$ for three hours.

C. Mounting of roots

Irradiated roots are afixed to Teflon holders using Kerr sticky wax and mounted onto a Grabenstetter cross-brushing machine (cf. Grabenslatter, R. J., et. al., J. Dent. Res. 37,1060 (1958)). Toothbrushes used throughout the test are 50-Tuft, medium, flat, "Pepsodent" toothbrushes.

D. Preconditioning the dentin surfaces

Prior to initial test run with the freshly mounted, irradiated roots they are brushed with a reference slurry (10g calcium pyrophosphate + 50ml of a 0.5% CMC-10% glycerine solution) for 10,000-15,000 brush strokes.

E. Test run

The dentin samples are conditioned with the reference slurry (Step D) for 1500 brush strokes at the beginning, during and end of each test run. Test run consists of brushing dentin samples for 1500 brush strokes with a slurry of test product (25g dentifrice + 50ml deionized or distilled water).

F. Preparation of correction factors

The correction factors are prepared by dissolving dentin chips from Step B in 5ml conc. HCl brought to a volume of 250ml with distilled water. One ml of this solution is added to test pastes and reference slurries which are prepared similarly to those in Step E, and then neutralized with 1 N NaOH.

Radioactive Tracer Counting

The radioactivity of the slurry samples (1.0ml) is determined with an Intertechnique SL-30 liquid scintillation counter. Alternate counting procedure: 3ml aliquots of each slurry are transferred to stainless steel, flat-bottom 1 inch × 5/16 inch planchets and counted using Nuclear Chicago Geiger Counting System.

Calculations

The radioactive dentin abrasion value (RDA) for a particular paste will be the ratio of the average corrected counts for that paste to the average count for the reference multiplied by 500. The reference abrasive is given an arbitrary dentin abrasion value of 500 units.

The following toothpastes were prepared in the laboratory:

EXAMPLE 1

| Ingredients | Percent |
| --- | --- |
| Precipitated amorphous silica | 12.00 |
| Alpha alumina trihydrate | 20.00 |
| Flavor | 0.88 |
| Sodium lauryl sulfate (21%) plus glycerin (79%) mixture | 5.50 |
| Liquid humectant/binder mix | 61.62 |

EXAMPLE 1-continued

| | Percent |
| --- | --- |
| Sorbitol (70% aqueous | 35.00 |
| Distilled water | 22.20 |
| Carboxymethyl cellulose 9M | 0.95 |
| Saccharin | 0.14 |
| Polyethylene glycol 1540 | 3.00 |
| Sodium benzoate | 0.08 |
| Titanium dioxide | 0.25 |
| | 61.62 |
| Total | 100.00 |

The liquid humectant/binder mix was prepared by the simple addition of all ingredients to the water/sorbitol solution, and stirring until all soluble components were dissolved and the titanium dioxide was thoroughly dispersed.

The powders were then mixed in a paste mixer with the liquid humectant/binder mix until a stiff paste was obtained.

EXAMPLE 1

Next, the detergent in gylcerin was added and mixed in thoroughly. The paste so obtained was deaerated by subjecting it to a vacuum, and carefully packed into uncoated collapsible aluminum tubes, avoiding incorporation of air.

The toothpaste was then subjected to the Luster and Dentin Abrasion Tests and determined to have the following values:

| Luster value: | 56 |
| --- | --- |
| Dentin abrasion value: | 357 |

When this toothpaste was stored under accelerated aging conditions, i.e., one month at 50° C, it developed a porous, cheesy texture, and the aluminum tube wall became darkened and nonuniform, i.e., signs of potential corrosion became evident.

EXAMPLE 2

The product of Example 1 was prepared, except that the liquid humectant/binder mix was reduced to 60.62%, and 1% dicalcium phosphate dihydrate was added with the powders. Luster and Dentin Abrasion tests were run and the results are itemized as follows:

| Luster value: | 59 |
| --- | --- |
| Dentin abrasion value: | 361 (average of 5 determinations) |

On storage of this dentifrice for one month at 50° C, no significant deterioration of either toothpaste or tube could be detected. The aluminum tube wall remained intact and the toothpaste retained its luster effect.

Example 3

As Example 2, except 1% of the anhydrous dicalcium phosphate was used instead of the dihydrate. Luster and Dentin Abrasion values are as follows:

| Luster value: | 57 |
| --- | --- |
| Dentin abrasion value: | 409 |

The stability of this dentifrice was acceptable and the dentifrice did not adversely affect the tube.

EXAMPLE 4

The product of Example 2 was prepared, except that the dicalcium phosphate dihydrate level was raised to 5% and the liquid humectant/binder mix lowered by the same amount.

| Luster value: | 58 |
|---|---|

The stability of product and condition of tube were both excellent, as measured by storage at 50° C for one month.

EXAMPLES 5-7

Products were prepared varying the levels of alpha alumina trihydrate and precipitated amorphous silica, and the results are shown below in Table 3:

TABLE 3

|  |  | Example 5 | Example 6 | Example 7 |
|---|---|---|---|---|
|  |  | 6823 | 6824 | 6826 |
| Precipitated Amorphous Silica |  | 10.00 | 10.00 | 20.00 |
| Alpha Alumina Trihydrate |  | 10.00 | 30.00 | 10.00 |
| Dicalcium Phosphate-Dihydrate |  | 1.00 | 1.00 | 1.00 |
| Dicalcium Phosphate-Anhydrous |  | — | — | — |
| Flavor |  | 0.88 | 0.88 | 0.88 |
| Sodium Lauryl Sulfate (21%) plus Glycerin (79%) mixture |  | 5.50 | 5.50 | 5.50 |
| Liquid Humectant/Binder Mix |  | 72.62 | 52.62 | 62.62 |
|  | % |  |  |  |
| Sorbitol (70% Aqueous) | 56.91 |  |  |  |
| Distilled Water | 35.88 |  |  |  |
| Carboxymethyl Cellulose 9M | 1.49 |  |  |  |
| Saccharin | 0.23 |  |  |  |
| Polyethylene Glycol 1540 | 4.95 |  |  |  |
| Sodium Benzoate | 0.13 |  |  |  |
| Titanium Dioxide | 0.41 |  |  |  |
|  | 100.00 |  |  |  |
|  |  | 100.00 | 100.00 | 100.00 |
| Luster Value |  | 58 | 59 | 57 |
| RDA Value (Dentin Abrasion Value) |  | 251 | 416 | 276 |

EXAMPLE 8

To demonstrate the low abrasiveness of the precipitated amorphous silica, the product of Example 7 was prepared in the same manner, except that the alpha-alumina trihydrate was replaced with an equal amount by weight of the liquid humectant/binder mix. The paste so obtained was too thick to be accepted as a dentifrice. Nevertheless, when subjected to the Dentin Abrasion Test, the toothpaste evidenced a dentin abrasion value of 150.

What is claimed is:

1. A toothpaste composition for incorporation into an uncoated aluminum tube that provides an improved luster to tooth enamel comprising
   a. from 10% to 30% of alpha alumina trihydrate having an average particle size of from about 6.5 to about 8.5 microns;
   b. from 10% to 20% of a precipitated amorphous silica having a low abrasive capacity; and
   c. a stabilizing agent of about 1 to 5% dicalcium phosphate dihydrate or about 0.5 to 2% anhydrous dicalcium phosphate;
   said stabilizing agents being effective to stabilize components (a) and (b) against corrosion of uncoated aluminum tubes.

2. A toothpaste composition in accordance with claim 1 wherein the alpha alumina trihydrate is present in an amount of from 20 to 25% by weight of the total composition.

3. A toothpaste composition in accordance with claim 2 wherein the precipitated amorphous silica is present in a range from 10 to 15% based on the total weight of the composition.

4. A toothpaste composition in accordance with claim 3 wherein the stabilizing agent is dicalcium phosphate dihydrate said stabilizing agent being present in an amount of from about 1 to 2% by weight, based on the total weight of the composition.

5. A toothpaste composition in accordance with claim 3 wherein the stabilizing agent is anhydrous dicalcium phosphate, said stabilizing agent being present in an amount of from 1 to 1.5% by weight based on the total weight of the composition.

* * * * *